United States Patent [19]

Normandin

[11] Patent Number: 4,871,652

[45] Date of Patent: Oct. 3, 1989

[54] PHOTOGRAPHIC SILVER HALIDE MATERIAL AND PROCESS

[75] Inventor: Sharon E. Normandin, Macedon, N.Y.

[73] Assignee: Eastman Kodak Company, Rochester, N.Y.

[21] Appl. No.: 241,512

[22] Filed: Sep. 7, 1988

[51] Int. Cl.$^4$ .......................... G03C 7/36; G03C 7/38
[52] U.S. Cl. ..................................... 430/387; 430/386; 430/543; 430/556; 430/557; 430/548; 430/558
[58] Field of Search ............... 430/386, 387, 543, 556, 430/557, 558 R, 538 A, 548

[56] References Cited

U.S. PATENT DOCUMENTS

| | | | |
|---|---|---|---|
| 2,380,809 | 7/1945 | Verkinderen et al. | 430/556 |
| 2,435,173 | 1/1948 | Bavley | 430/558 |
| 2,600,788 | 6/1952 | Loria et al. | 430/554 |
| 2,897,079 | 7/1959 | DeCat et al. | 430/558 |
| 3,502,468 | 3/1970 | Rogers | 430/218 |

FOREIGN PATENT DOCUMENTS

| | | | |
|---|---|---|---|
| 1247493 | 9/1971 | United Kingdom | 430/476 |
| 1252418 | 11/1971 | United Kingdom | 430/555 |

OTHER PUBLICATIONS

Research Disclosure, Dec. 1978, Item No. 17643, vol. 176, Kenneth Mason Publications Ltd., Hampshire England.

*Primary Examiner*—Richard L. Schilling
*Attorney, Agent, or Firm*—Richard E. Knapp

[57] ABSTRACT

Novel cyano substituted photographic couplers are represented by the formula:

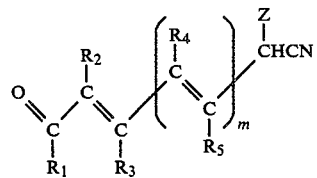

wherein m, $R_1$, $R_2$, $R_3$, $R_4$, $R_5$ and Z are as defined in the specification. These couplers enable effective magenta dye formation upon reaction with an oxidized color photographic silver halide developing agent. The couplers are useful in photographic silver halide materials and processes.

6 Claims, No Drawings

PHOTOGRAPHIC SILVER HALIDE MATERIAL AND PROCESS

This invention relates to novel cyano substituted photographic couplers and to photographic silver halide materials and processes using such couplers.

Color images are customarily obtained in the photographic art by reaction between the oxidation product of a silver halide color developing agent and a dye-forming coupler. Pyrazolone couplers, such as

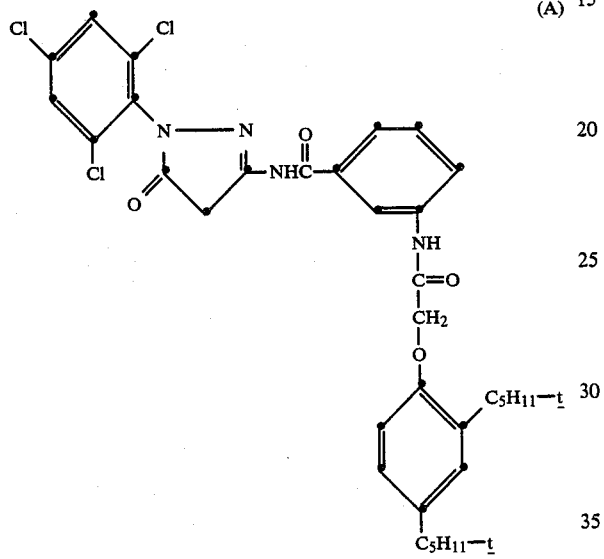

(A)

are useful for forming magenta dye images, such as described in U.S. Pat. No. 2,600,788. Such pyrazolones are very reactive couplers. However, this high reactivity has caused decreased efficiency of the dye forming reaction due to, for example, side reactions that can happen, such as reaction with formaldehyde present during photographic processing. Pyrazolotriazole couplers have been more effective to resist the side reactions of formaldehyde, but such couplers often suppress development because of their undesirably high affinity for silver halide and they require difficult methods of synthesis such as described in U.K. Patents 1,247,493 and 1,252,418.

It has been desirable to provide a new class of couplers that have less affinity for silver halide and provide high reactivity with the capability to provide dyes that are shifted in hue hypsochromically compared to known pyrazolone couplers. It has also been desirable to provide such new couplers that can be prepared by simpler methods of synthesis than those required for preparation of pyrazolotriazole couplers.

It has been found that magenta dye-forming couplers that enable high reactivity and a hue shift hypsochromically for the dye formed are cyano substituted dye-forming couplers represented by the structural formula (I):

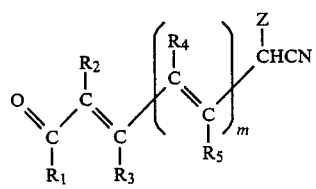

(I)

wherein
  m is 0 or 1;
  $R_1$ is unsubstituted or substituted alkyl or aryl;
  $R_2$, $R_3$, $R_4$ and $R_5$ are individually hydrogen or unsubstituted or substituted alkyl or aryl, or $R_3$ with at least one of $R_1$ and $R_5$ represents the atoms necessary to form unsubstituted or substituted 5- or 6-member carbocyclic or heterocyclic rings;
  Z is hydrogen, or a coupling-off group, particularly $-OR_6$, $-SR_7$, chlorine, or bromine; and
  $R_6$ and $R_7$ individually are unsubstituted or substituted alkyl, aryl, or heterocyclic groups.

Particularly useful cyano-substituted couplers, as described, are represented by the structural formulas (II), (III), and (IV):

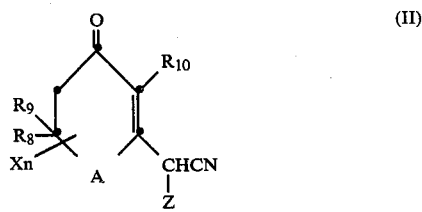

(II)

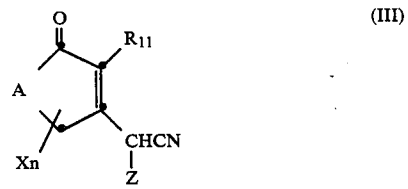

(III)

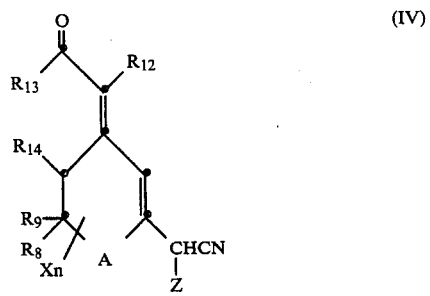

(IV)

wherein
  each X is individually a cyano, alkyl or aryl group;
  n is 0 to 4;
  $R_8$ and $R_9$ are individually alkyl containing 1 to 5 carbon atoms, particularly methyl, or aryl, such as phenyl or substituted phenyl; or hydrogen;
  $R_{10}$, $R_{11}$, $R_{12}$ and $R_{14}$ are as defined for $R_2$;
  $R_{13}$ is as defined for $R_1$ or with $R_{14}$ represents the atoms necessary to form a 5- or 6-member ring, particularly a carbocyclic or heterocyclic ring;
  A is a ring atom selected from O, N, or C; and
  Z is hydrogen or a coupling-off group as defined above.

Other preferred couplers, as described, are cyano-substituted couplers represented by the structural formula (V):

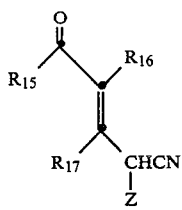

wherein $R_{15}$ is unsubstituted or substituted alkyl or aryl;

$R_{16}$ and $R_{17}$ are individually hydrogen or unsubstituted or substituted alkyl or aryl; and Z is hydrogen or a coupling-off group as defined above.

The described alkyl groups can be unsubstituted or optionally substituted with groups that do not adversely affect the properties of the coupler or the dye formed. The alkyl group can, for example, contain from 1 to 30 carbon atoms, such as methyl, ethyl, propyl, n-butyl, t-butyl, pentyl, octyl, eicosyl, triacontyl. The alkyl group can be optionally substituted with, for example, halogen, (such as chlorine, bromine, or fluorine), hydroxy, carboxy, cyano, nitro, alkoxy, sulfonamido, sulfamyl, amino, carbonamido, sulfonyl, aryloxy, ureido, alkyl, aryl, (such as phenyl and naphthyl), or phenolic, carbocyclic, and heterocyclic substituent groups.

The described aryl groups can also be unsubstituted or optionally substituted with groups that do not adversely affect the properties of the couplers or the dyes formed from the couplers. The aryl group can contain, for example, 6 to 30 carbon atoms. Phenyl and napthyl groups are illustrative aryl groups. The substituents can be, for example, halogen, (such as chlorine, bromine, or fluorine); alkyl, such as alkyl containing 1 to 30 carbon atoms, for example, methyl, ethyl, propyl, n-butyl, t-butyl, pentyl, eicosyl, or triacontyl; hydroxy, carboxy, cyano, nitro, alkoxy, sulfonamido, sulfamyl, amino, carbonamido, sulfonyl, aryloxy, ureido, alkyl, (such as alkyl containing 1 to 30 carbon atoms, for example methyl, ethyl, propyl, n-butyl, t-butyl, eicosyl, and triacontyl), aryl, (such as phenyl and naphthyl); carboxylic esters and heterocyclic groups.

Substituents on the described couplers can include ballast groups and coupler moieties that are known to be useful in the photographic art.

The coupling position of the described couplers, that is the carbon atom linked to the cyano group, can be substituted with a coupling-off group known in the photographic art. Examples of specific coupling-off groups include:

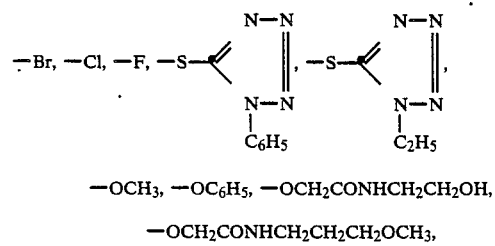

—OCH$_3$, —OC$_6$H$_5$, —OCH$_2$CONHCH$_2$CH$_2$OH,

—OCH$_2$CONHCH$_2$CH$_2$CH$_2$OCH$_3$,

-continued

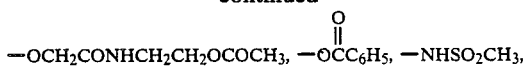

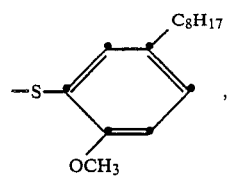

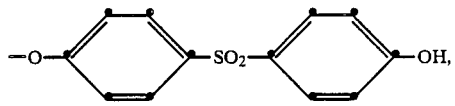

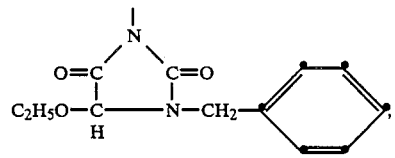

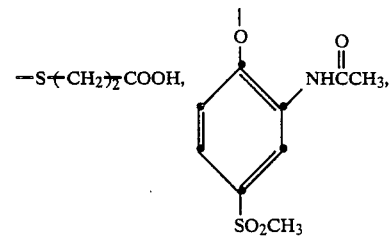

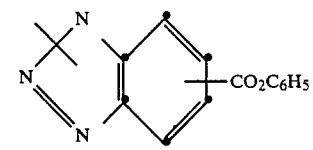

The coupler as described can contain a ballast group that is an organic radical of such size and configuration as to confer on the coupler molecule sufficient bulk to render the coupler substantially non-diffusible from the layer in which it is coated in a photographic element. Couplers as described can be attached to ballast groups or to polymeric chains through one or more of the described R groups or through the coupling-off group. For example, one or more of the couplers can be attached to the same ballast group. Representative ballast groups include unsubstituted or substituted alkyl or aryl groups containing 8 to 32 carbon atoms. Representative substituents include alkyl, aryl, alkoxy, aryloxy, alkylthio, arylthio, hydroxy, halogen, alkoxycarbonyl, aryloxycarbonyl, carboxy, acyl, acyloxy, amino, anilino, carbonamido, carbamoyl, alkanesulfonyl, arenesulfonyl, sulfonamido and sulfamyl groups. The alkyl portion of these substituents can contain, for example, 1 to 30 carbon atoms. The aryl portion of these substituents can contain, for example, 6 to 30 carbon atoms.

The couplers as described can be used in ways and for purposes that dye-forming couplers have been used in the photographic art.

Examples of such cyanomethyl substituted couplers include:

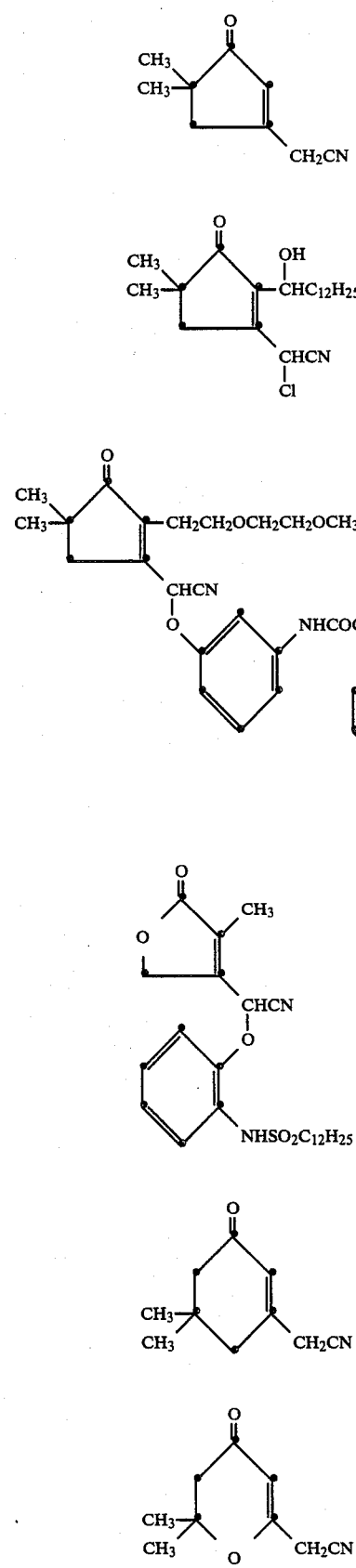
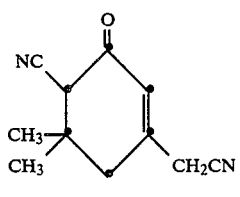
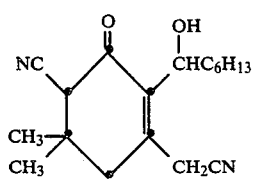
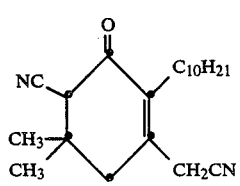
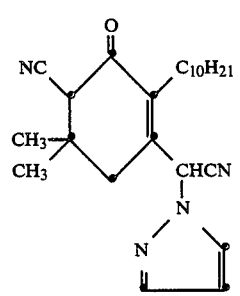
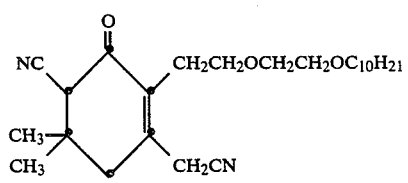
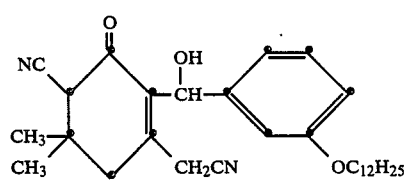
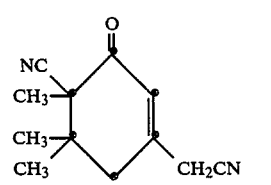

-continued

14. 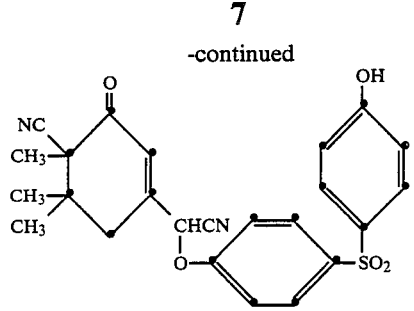

15. 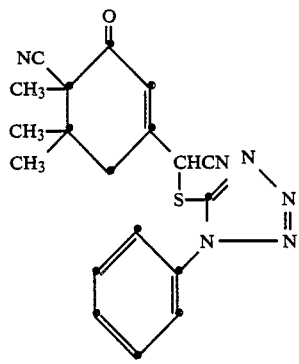

16. 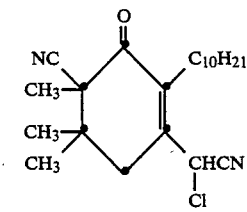

17. 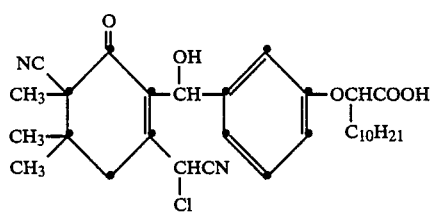

18. 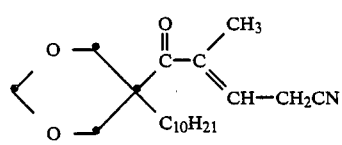

19. 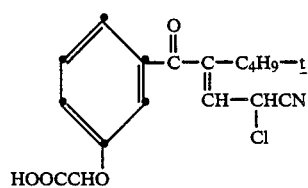

20. 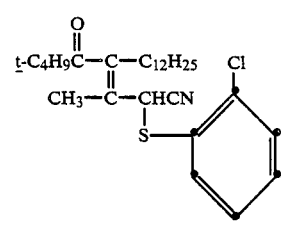

-continued

21. 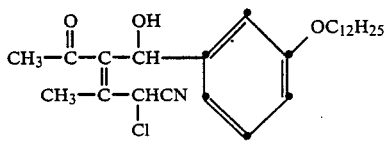

22. 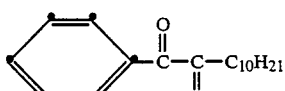

23. 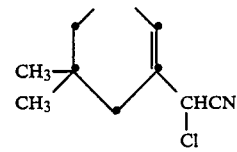

The cyano substituted couplers of the invention are prepared by simple methods of synthesis. The following method is representative of the synthesis of couplers of the invention:

Ethyl cyanoacetate (A) is heated in refluxing acetone (B) in the presence of potassium carbonate to form a single major cyano substituted compound ($P_1$). This results from the condensation of two molecules of the isopropylidene derivative (C) as shown in the following scheme I. Acid catalyzed hydrolysis of the ethyl ester is accompanied by decarboxylation to produce 3-cyanomethyl-6-cyano-5,5-dimethyl-2-cyclohexenone ($P_2$). This product is isolated and purified by methods known in the organic synthesis art.

Scheme I

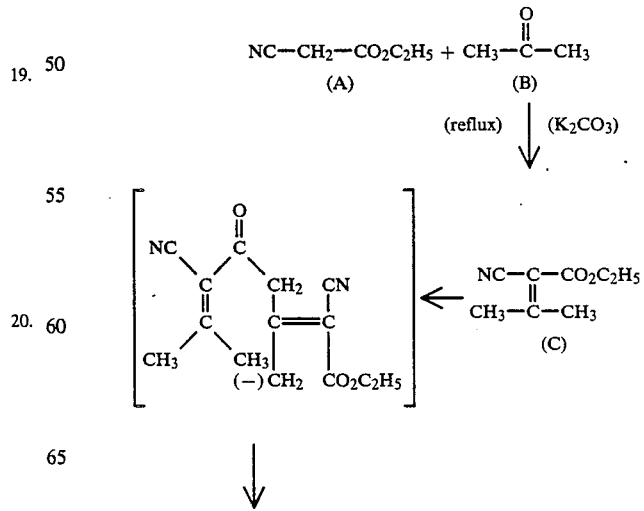

-continued
Scheme I

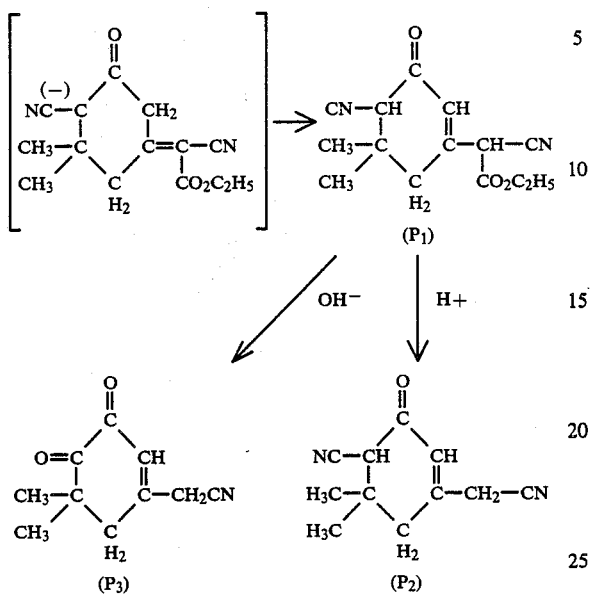

If compound $P_1$ is treated with hydroxide rather than acid hydrolyzed, a compound $P_3$ having two carbonyl groups is formed rather than compound $P_2$. Both of these compounds can react with oxidized photographic silver halide color developing agent. The structure of the couplers can be identified by means known in the organic compound analytical art, such as high resolution mass spectroscopy, or nuclear magnetic resonance spectroscopy.

The coupler $P_2$ does not form an insoluble silver salt indicating either that this compound does not form a silver salt or that the salt formed is soluble.

A dye is formed from a coupler of the invention by reaction of the coupler with oxidized photographic silver halide developing agent, preferably a phenylenediamine color photographic developing agent. This reaction is illustrated by the following reaction scheme in which compound 7 is reacted with an oxidized phenylenediamine photographic silver halide color developing agent:

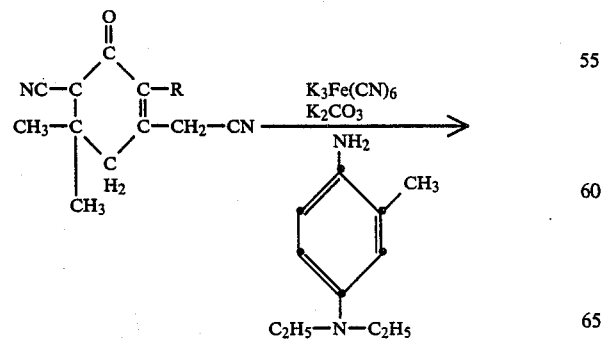

Compd. 7 R = H
Compd. 9 R = $C_{10}H_{21}$

-continued

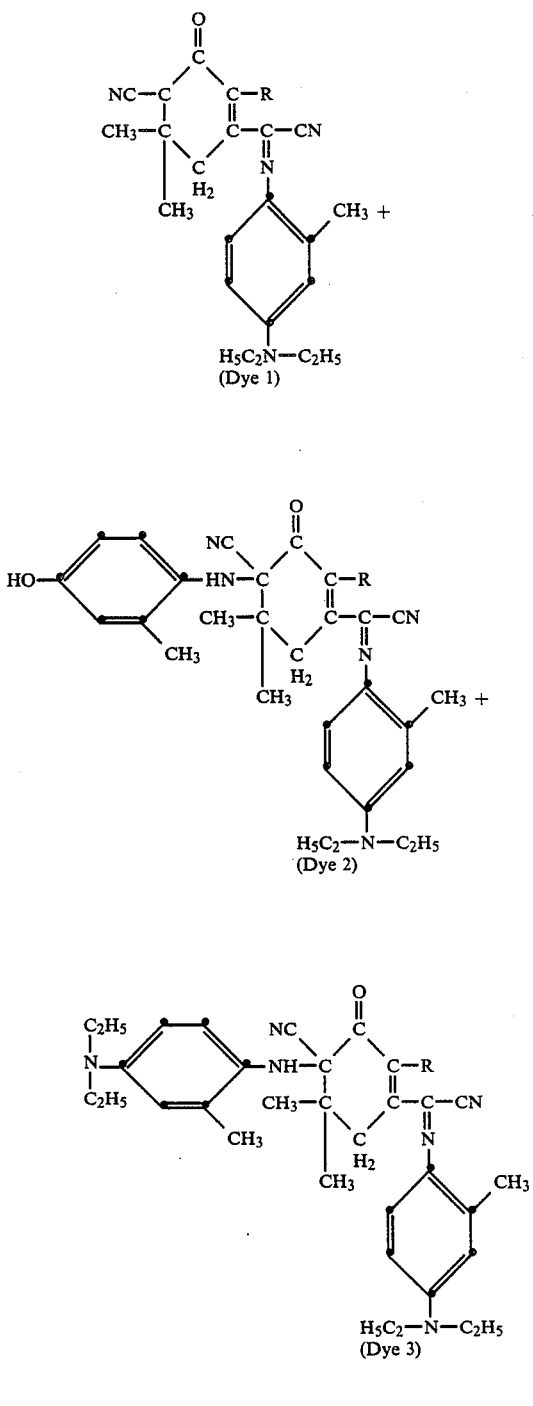

Isolation of the dye products and analysis, such as by mass spectral analysis, indicated that Dyes 1, 2 and 3 were formed. The major dye formed was Dye 3. Upon further reaction the dyes formed the following dye:

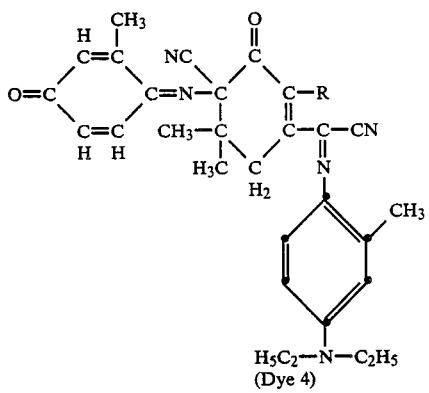

(Dye 4)

wherein R is as defined. It was found that treatment of the starting coupler with a limited concentration of the oxidized color developer (molar ratio of oxidized developer/coupler=0.21) results in the exclusive formation of Dye 3. However, when the starting coupler is treated with a large excess (ten fold excess) of the oxidized color developer then the dye formed is Dye 4. The visible spectra of the dyes formed were measured in butyl acetate. Dyes 1, 2 and 3 have a maximum absorption at 520 nm. The Dye 4 has a maximum absorption at 545 nm. Similar dyes, but of shorter wavelength absorption, were obtained from compound 9.

When the 6-cyano group is deleted from compounds 7 or 9, only one dye is formed. This corresponds to Dye 1 without the 6-cyano group.

Another illustrative preparation is the synthesis of compound 13 represented by the formula:

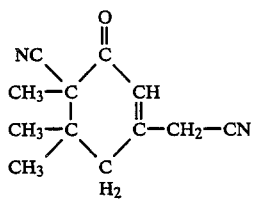

Compound 13

The preparation of this coupler comprises the reaction of compound 7 with two molar equivalents of lithium di-isopropylamide at −78° C., followed by reaction of the product with methyl iodide. The alkylation reaction rate can be increased by carrying the reaction out at 0° C.

The following examples further illustrate the invention.

Synthesis Example 1

Synthesis of Compound 7

Ethyl cyanoacetate (0.26 moles) was dissolved in acetone (250 mL) and potassium carbonate (0.29 moles) was added. The resulting suspension was heated to reflux for 4 hours, then cooled to room temperature and solvent was evaporated under reduced pressure. The resulting orange solid was dissolved in methanol (50 mL) and an equal volume of 6N aqueous hydrochloric acid was added. After the resulting mixture had been heated to reflux for 24 hours, it was cooled to room temperature, concentrated at reduced pressure, and the residue was partitioned between methylene chloride and water. The organic layer was dried by filtration through anhydrous magnesium sulfate and solvent was evaporated under reduced pressure. Trituration with hexane gave 14.2 g compound 7 (58% yield) as a tan solid, m.p. 101°–102° C. The expected structure was confirmed by proton nmr and mass spectral data:

nmr (CDCl$_3$); δ,ppm:
1.20 (s, 3H), 1.35 (s, 3H), 2.45 (dd, 2H), 3.36 (s, 2H), 3.44 (s, 1H), 6.28 (s, 1H).

Mass Spectrum: Calculated for $C_{11}H_{12}N_2O_4$—188.2300; observed—188.0941.

Synthesis Example 2

Synthesis of Compound 9

To a solution of diisopropylamine (31.5 mmol) in tetrahydrofuran (31.5 mL) at 0° C. was added a 2.2M solution of n-butyllithium in hexane (31.5 mmol). After stirring for 15 minutes at 0° C., this solution was cooled to −78° C. and a solution of compound 7 (30 mmol) in tetrahydrofuran (30 mL) was added dropwise. The resulting orange solution was stirred at −78° C. for 20 minutes, at which time iododecane (30 mmol) was added rapidly and the temperature was allowed to warm to 0° C. After 6 hours the pH was adjusted to 6.0 by the addition of 6N aqueous hydrochloric acid and the mixture extracted with methylene chloride. The organic layer was filtered through anhydrous magnesium sulfate and concentrated under reduced pressure to give an oil which was purified by chromatography on silica gel to give 3.6 g of a white solid product (35% yield), m.p. 49°–50° C. The expected structure for compound 9 was confirmed by proton nmr and mass spectral data:

nmr (CDCl$_3$); δ,ppm:
0.90 (t, 3H), 1.20 (s, 3H), 1.25–1.30 (broad s, 16H), 1.35 (s, 3H), 2.35–2.40 (m, 2H), 2.6 (dd, 2H), 3.40 (s, 2H), 3.45 (s, 1H).

Mass Spectrum: m/e 328.

Example 1

Rate of dye formation of preferred compound of the invention

The rate of dye formation of compound 7 was measured using aqueous stock solutions A through D and stopped-flow kinetics described as follows:

Stock Solution A: A solution $1\times10^{-3}$M in compound 7 containing 67% Triton X-100 (Triton X-100 is a trademark)

Stock Solution B: A carbonate buffer solution of pH 10.0 and ionic strength of 1.5

Stock Solution C: $4\times10^{-4}$M potassium ferricyanide in water

Stock Solution D: $4\times10^{-5}$M 4-amino-3-methyl-N,N-diethylaniline sulfate.

Equal volumes of solutions A and B were combined and placed in one syringe of the stopped-flow apparatus. A second syringe contained a mixture of equal volumes of stock solutions C and D. The contents of the two syringes were combined and the rate of dye formation was observed spectrophotometrically at λmax.

The procedure was repeated with a second solution of compound 7 prepared by diluting solution A with 6% Triton X-100 to give a solution $5\times10^{-4}$M in coupler. Log kc$^\theta$ was calculated from k observed and the results averaged. The rates for the comparison couplers were obtained in an analogous manner by substituting compounds C-1, C-2 and C-3 for compound 7 in solution A. Results are shown in Table I.

TABLE I

|  | Compd. No. | log kc$^\theta$ | λmax (BuOAc)(nm) |
|---|---|---|---|
| Example 1 | 7 | 4.50 | 519 |
| Comparison A | C-1* | 2.33 | 530 |
| Comparison B | C-2* | 4.59 | 530 |
| Comparison C | C-3* | 4.80 | — |

*Structures of comparison couplers

C-1

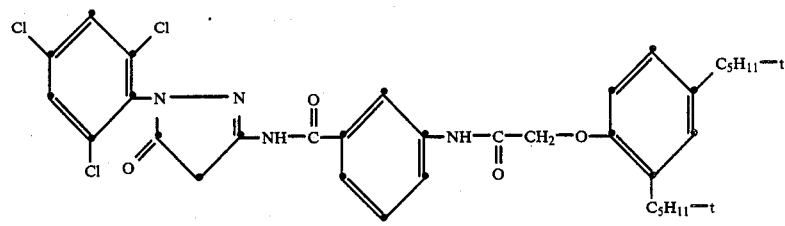

C-2

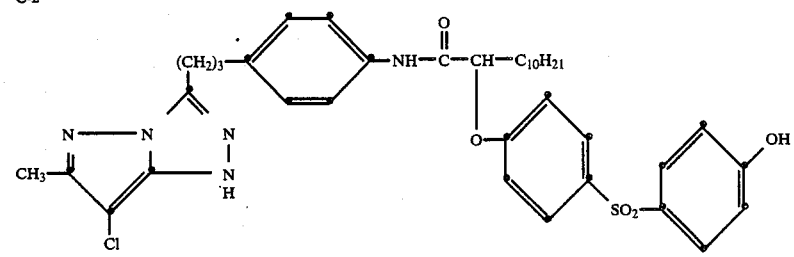

C-3

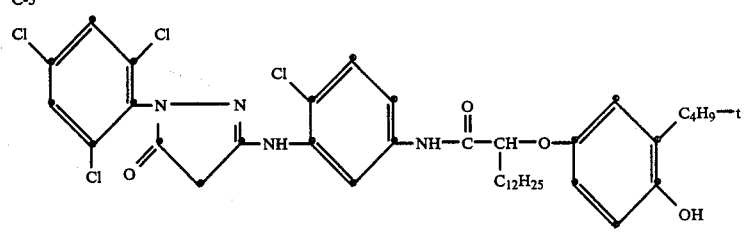

The data show that the inventive compound 7 reacts with oxidized color developer to form a magenta dye at a rate greater than that of well-known comparison coupler C-1. Surprisingly, the reactivity of compound 7 is very close to that of active couplers C-2 and C-3, although compound 7 does not rely on the benefits of being 2-equivalent or having a phenolic ballast group.

Example 2

Photographic Element Comprising Coupler of the Invention

Photographic elements were prepared by coating a cellulose acetate film support with a photosensitive layer containing a silver halide emulsion at 0.86 g Ag/m$^2$, exposing these strips through a graduated density test object and processing in DK50 for 6 minutes at 68° F. These strips were then fixed, washed, bleached, washed and dried to obtain a stepped silver halide image. Developing solutions were prepared by dissolving 1.937 mmol of each coupler designated in Table II in 2.5 mL of 2-methyl-2,4-pentanediol and 2.5 mL of 3.5M NaOH solution and adding this solution to 500 mL of solution A prepared as follows:

| | |
|---|---|
| Nitrilotris (methylene phosphonic acid) pentasodium salt (37% aqueous solution) | 3 mL |
| Sodium sulfite | 5 g |
| Potassium iodide | 0.12 g |
| Sodium bromide | 0.80 g |
| Sodium sulfate | 20 g |
| Sodium hydroxide | 3.7 g |
| 4-amino-3-methyl-N—ethyl-N—β-(methane sulfonamido)-ethylaniline sulfate hydrate | 1.9 g |
| Carbowax 3350 | 1 g |
| Sodium thiocyanate | 1 g |
| 3,6-dithiaoctane-1,8-diol | 1.2 g |
| Sodium carbonate | 25 g |
| Sodium bicarbonate | 6 g |
| Water to 1 liter and pH adjusted to 10.75 | |

The strips obtained above were exposed to light, then processed in this developing solution for 4 minutes at 100° C., bleached, washed, fixed, washed and dried. Dye hues were obtained from spectrophotometric curves by measuring the maximum absorption peak (λmax) normalized to 1.0 density. Half-band width (HBW) is reported as the width of each curve at 0.5 density. Density at 425 nm was measured directly from these curves. Results are shown in Table II.

TABLE II

|  | Compd. No. | λmax (HBW) | Density at 425 nm |
|---|---|---|---|
| Example 2 | 7 | 532 (125) | 0.22 |

TABLE II-continued

| Compd. No. | λmax (HBW) | Density at 425 nm |
|---|---|---|
| Comparison D | C-4* | 539 (103) | 0.32 |

*Structures of comparison coupler C-4

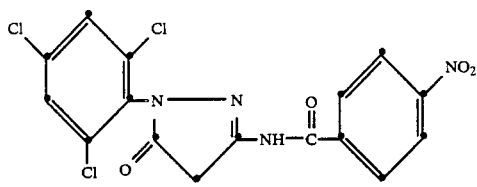

The data show that the inventive compound 9 reacts in a photographic element to form a magenta dye of hue comparable to the comparison coupler C-4. In addition, the inventive compound shows an advantage in reduced undesirable blue light absorption in the 425 nm region.

Example 3

Photographic Element Comprising Coupler of the Invention

Photographic elements were prepared by coating a cellulose acetate-butyrate film support with a photosensitive layer containing a silver bromoiodide emulsion at 0.91 g Ag/m$^2$, gelatin at 3.77 g/m$^2$, and one of the couplers designated in Table III dispersed in half its weight of tricresyl phosphate and coated at 1.62 mmol/m$^2$. The photosensitive layer was overcoated with a layer containing gelatin at 1.08 g/m$^2$ and bis-vinyl-sulfonyl methyl ether at 1.75 weight percent based on total gelatin.

Samples of each element were imagewise exposed through a graduated density test object and processed at 40° C., employing the following color developing solution, then stopped, bleached, fixed, washed and dried to produce stepped magenta dye images.

| Color Developer | |
|---|---|
| K$_2$SO$_3$ | 2.0 g |
| K$_2$CO$_3$ | 30.0 g |
| KBr | 1.25 g |
| KI | 0.6 mg |
| 4-amino-3-methyl-N—ethyl-N—β-hydroxyethylaniline sulfate | 3.55 g |
| Water to 1.0 liter, pH 10.0 | |

Dye hues were obtained from spectrophotometric curves by measuring the maximum absorption peak (λmax) normalized to 1.0 density. The density was measured at λmax and the amount of developed silver was measured by x-ray fluorescence. The results are shown in Table III.

TABLE III

| | Compd. No. | λmax (HBW) | Density at λmax | Developed Ag |
|---|---|---|---|---|
| Example 3 | 9 | 511 (133) | 0.94 | 0.70 g/m$^2$ |
| Comparison A | C-1 | 556 (92) | 1.11 | 0.63 g/m$^2$ |
| Comparison B | C-2 | 556 (89) | 1.85 | 0.49 g/m$^2$ |
| Comparison C | C-3 | 545 (84) | 0.99 | 0.60 g/m$^2$ |

The data show that the inventive compound 9 reacts in a photographic system to form a magenta dye of density comparable to that of comparison compound C-3. In addition, inventive compound 9 shows the distinct advantage of increased developed silver.

The photographic elements can be single color elements or multicolor elements. In a multicolor element, the dye-forming coupler of this invention would usually be associated with a green-sensitized emulsion, although it could be associated with an unsensitized emulsion or an emulsion sensitized to a different region of the spectrum. Multicolor elements typically contain image dye-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsion sensitive to each of the three primary regions of the spectrum can be disposed as a single segmented layer.

A typical multicolor photographic element comprises a support bearing a cyan image dye-forming unit comprised of at least one red-sensitive silver halide emulsion layer having associated therewith at least one cyan dye-forming coupler, a magenta image dye-forming unit comprising at least one green-sensitive silver halide emulsion layer having associated therewith at least one magenta dye-forming coupler, and a yellow image dye-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of materials for use in the emulsions and elements of this invention, reference will be made to Research Disclosure, December 1978, Item No. 17643, the disclosures of which are incorporated herein by reference. This publication will be identified hereafter by the term "Research Disclosure".

The silver halide emulsions employed in the elements of this invention can be either negative-working or positive-working. Suitable emulsions and their preparation are described in Research Disclosure Sections I and II and the publications cited therein. Suitable vehicles for the emulsion layers of elements of this invention are described in Research Disclosure Section IX and the publications cited therein.

In addition to the couplers of this invention, the elements of the invention can include additional couplers known to be useful in the photographic art, such as described in Research Disclosure Section VII, paragraphs D, E, F and G and the publications cited therein. These couplers can be incorporated in the elements and emulsion as described in Research Disclosures of Section VII, paragraph C and the publications cited therein.

The photographic elements of this invention or individual layers thereof, can contain, for example, brighteners (see Research Disclosure Section V), antifoggants and stabilizers (See Research Disclosure Section VI), antistain agents and image dye stabilizers (see Research Disclosure Section VII, paragraphs I and J), light absorbing and scattering materials) see Research Disclosure Section VIII), hardeners (see Research Disclosure Section X), coating aids (see Research Disclosure Section XI), plasticizers and lubricants (see Research Disclosure Section XII), antistatic layers (see Research Disclosure Section XIII), matting agents (see Research Disclosure Section XVI) and development modifiers (see Research Disclosure Section XXI), colored masking couplers, and competing couplers.

The photographic elements can be coated on a variety of supports as described in *Research Disclosure* Section XVII and the references described therein.

Photographic elements can be exposed to actinic radiation, typically in the visible region of the spectrum, to form a latent image as described in *Research Disclosure* Section XVIII and then processed to form a visible dye image as described in *Research Disclosure* Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are
 4-amino-3-methyl-N,N-diethylaniline hydrochloride,
 4-amino-3-methyl-N-ethyl-N-β-(methanesulfonamido)ethylaniline sulfate hydrate,
 4-amino-3-methyl-N-ethyl-N-β-hydroxyethylaniline sulfate,
 4-amino-3-β-(methanesulfonamido)ethyl-N,N-diethylaniline hydrochloride and
 4-amino-N-ethyl-N-(2-methoxyethyl)-m-toluidine-di-p-toluenesulfonic acid.

With negative-working silver halide this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The invention has been described in detail with particular reference to preferred embodiments thereof, but it will be understood that variations and modifications can be effected within the spirit and scope of the invention.

What is claimed is:

1. A photographic element comprising a support bearing at least one photographic silver halide emulsion layer and a photographic coupler represented by the formula:

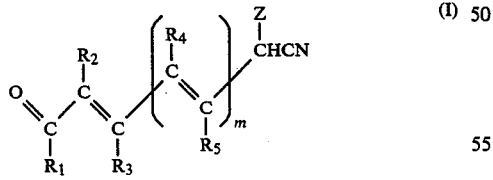

(I)

wherein
 m is 0 or 1;
 $R_1$ is unsubstituted or substituted alkyl or aryl;
 $R_2$, $R_3$, $R_4$ and $R_5$ are individually hydrogen or unsubstituted or substituted alkyl or aryl, or $R_3$ with at least one of $R_1$ and $R_5$ represents the atoms necessary to form unsubstituted or substituted 5- or 6-member carbocyclic or heterocyclic rings; and
 Z is hydrogen or a coupling-off group.

2. A photographic element as in claim 1 wherein the coupler is represented by the formula:

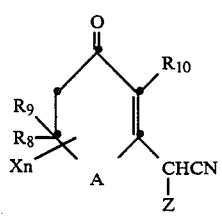

(II)

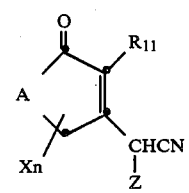

(III)

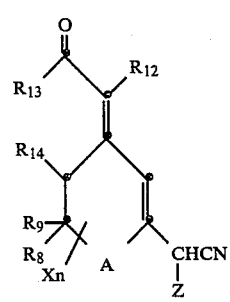

(IV)

wherein
 X is cyano, alkyl, or aryl;
 n is 0, 1, 2, 3 or 4;
 $R_8$ and $R_9$ are individually alkyl containing 1 to 5 carbon atoms or aryl; or hydrogen;
 $R_{10}$, $R_{11}$, $R_{12}$ and $R_{14}$ are individually hydrogen, or unsubstituted or substituted alkyl or aryl;
 $R_{13}$ is unsubstituted or substituted alkyl or aryl, or with $R_{14}$ represents the atoms necessary to form a 5- or 6-member carbocyclic or heterocyclic ring;
 A is a ring atom selected from O, N, or C; and
 Z is hydrogen or a coupling-off group.

3. A photographic element as in claim 1 wherein the coupler is represented by the formula:

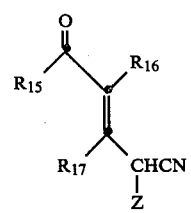

(V)

wherein
 $R_{15}$ is unsubstituted or substituted alkyl or aryl;
 $R_{16}$ and $R_{17}$ are individually hydrogen or unsubstituted or substituted alkyl or aryl; and
 Z is hydrogen or a coupling-off group.

4. A photographic element as in claim 1 wherein the coupler is:

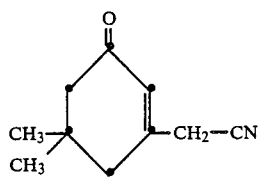

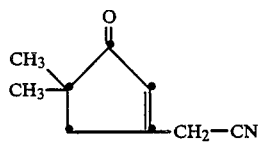

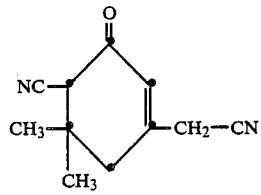

-continued

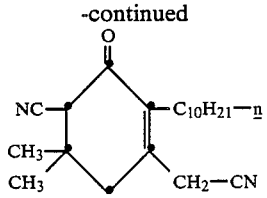

or

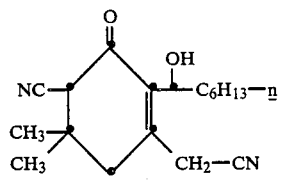

5. A process of forming a dye image in an exposed photographic silver halide element comprising a support bearing at least one photographic silver halide emulsion layer comprising developing the exposed photographic element in the presence of a dye-forming coupler as defined in claim 1.

6. A process as in claim 5 wherein the coupler is represented by the formula (II), (III) or (IV) as defined in claim 2.

* * * * *